United States Patent [19]

Keast et al.

[11] 4,254,655

[45] Mar. 10, 1981

[54] HYDRAULIC FILL VALVE

[75] Inventors: Larry G. Keast, Houston, Tex.;
Herbert D. Horton, Mayhill, N. Mex.

[73] Assignee: World Wide Oil Tools, Inc., Houston, Tex.

[21] Appl. No.: 82,978

[22] Filed: Oct. 9, 1979

[51] Int. Cl.³ ............................................. G01M 3/02
[52] U.S. Cl. ..................................................... 73/49.5
[58] Field of Search .................. 73/49.5, 49.6, 49.1, 73/49.8; 138/90

[56] References Cited

U.S. PATENT DOCUMENTS

| 1,422,522 | 7/1922 | Bareiss | 73/49.5 |
| 4,192,177 | 3/1980 | Crickard et al. | 73/49.5 |

Primary Examiner—Gerald Goldberg
Assistant Examiner—Joseph W. Roskos
Attorney, Agent, or Firm—Vinson & Elkins

[57] ABSTRACT

An improved method and apparatus for injecting hydraulic test fluid into a length of pipe is disclosed. Test fluid under low hydraulic pressure axially displaces a cylindrical fill valve against a retaining force. The test fluid fills the pipe through discharge ports in the side of the fill valve. The retaining force retracts the fill valve and closes the discharge ports when the pipe is full. A conduit through the fill valve then supplies high pressure hydraulic fluid for testing the internal strength of the pipe.

8 Claims, 3 Drawing Figures

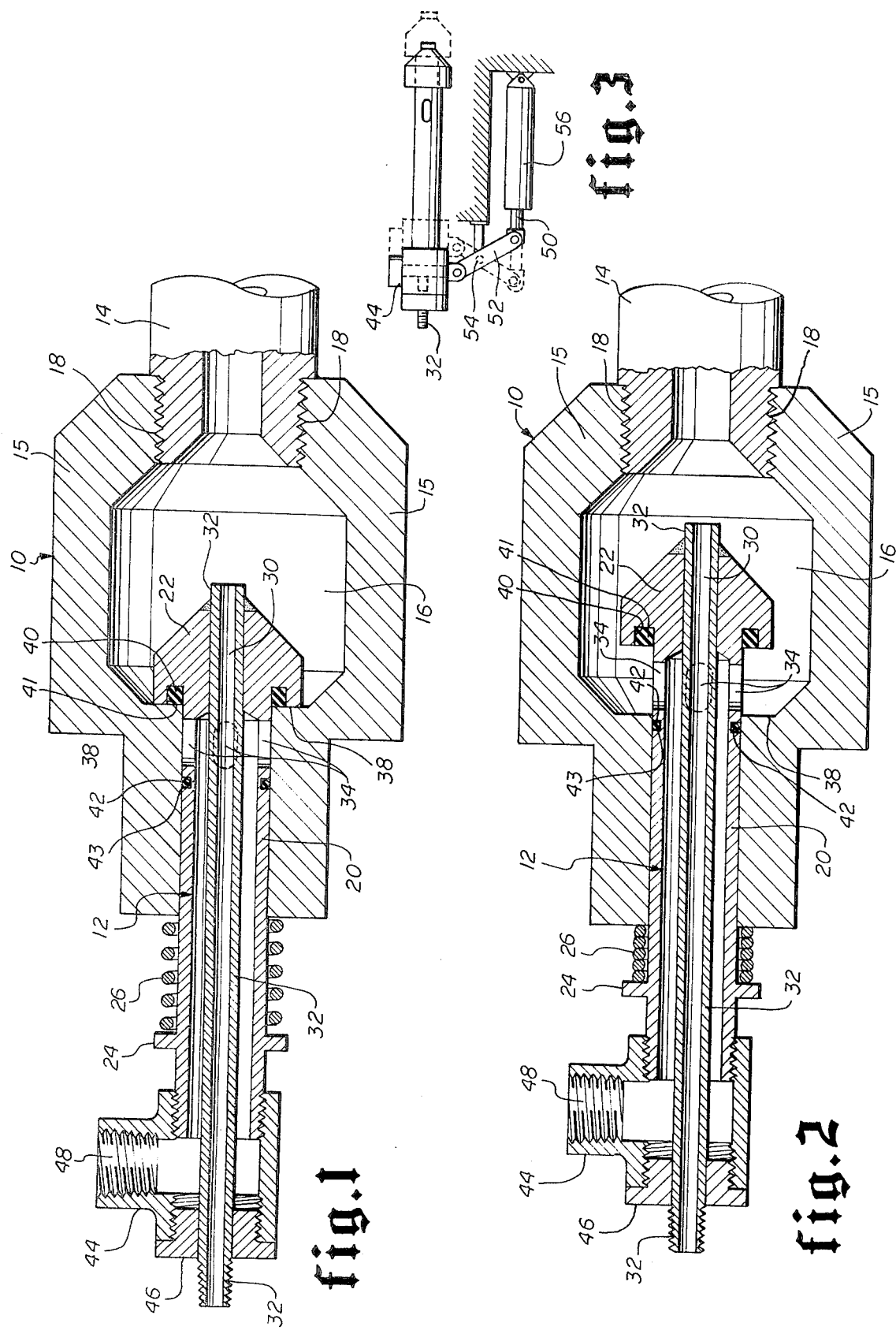

HYDRAULIC FILL VALVE

BACKGROUND OF THE INVENTION

This invention relates to the pressure testing of the internal strength of structures. More specifically, the invention relates to the means for supplying hydraulic test fluid to the interior of a length of pipe for hydraulically testing the internal strength of the pipe.

The process of hydraulically testing a length of pipe generally comprises fitting sealing devices into or around the ends of the pipe to be tested, admitting hydraulic fluid through an opening in one of the sealing devices, filling the pipe with hydraulic fluid, increasing the hydraulic pressure on the fluid to a predetermined value, checking the pipe for any cracks through which hydraulic fluid may be leaking under pressure, reducing the level of hydraulic fluid pressure on the fluid in the pipe after the test has been completed and removing the hydraulic test fluid from the pipe.

When the pipe is being filled with hydraulic fluid there is no necessity for the hydraulic fluid to be under very great pressure. Accordingly, the pipe is generally filled with hydraulic fluid under low pressure with the high hydraulic pressure being applied only during the testing phase of the process. The hydraulic fluid under relatively low pressure used to fill the pipe may be supplied from one source and the hydraulic fluid under high pressure to test the pipe may be supplied from another source.

It is an object of the present invention to provide improved means for supplying hydraulic fluid under low pressure and hydraulic fluid under high pressure into a length of pipe for hydraulically testing the strength of the pipe. The improved method of the present invention permits the design and operation of fully automatic pipe testing machinery.

Further objects and advantages of the present invention will become apparent in the course of the following detailed description and the appended claims, taken in conjunction with the accompanying drawings.

BRIEF DESCRIPTION OF THE DRAWINGS

In the drawings forming a part of this application in which is shown a preferred embodiment the invention may assume, and in which like parts are designated by like reference numerals, FIG. 1 illustrates a longitudinal cross section of the fill valve and housing of the present invention showing the construction and operating interaction of the various parts thereof when the fill valve is closed.

FIG. 2 illustrates a longitudinal cross section of the fill valve and housing of the present invention showing the construction and operating interaction of the various parts thereof when the fill valve is open.

FIG. 3 illustrates an alternative means for opening and closing the fill valve comprising a hydraulically operated piston and a pivot arm.

DESCRIPTION OF THE PREFERRED EMBODIMENTS

Referring to the drawings, the numeral 10 generally indicates the fill valve housing and the numeral 12 generally indicates the fill valve. Fill valve housing 10 is adapted to surround and hold fill valve 12 within an interior hollow portion of said housing 10. Fill valve 12 possesses the general form of an elongated hollow sleeve adapted to fit closely within said interior hollow portion of said housing 10.

Although fill valve housing 10 and fill valve 12 may be constructed in a number of different shapes, fill valve housing 10 and fill valve 12 in the preferred embodiment of the invention each possess the general shape of a hollow right circular cylinder. The outer diameter of the cylindrically shaped fill valve 12 is only slightly smaller than the inner diameter of the cylindrically shaped interior hollow portion of fill valve housing 10. Fill valve 12 is thus adapted to fit closely within said hollow portion of fill valve housing 10 and to move snugly forward and back longitudinally with respect to fill valve housing 10 along the congruent cylindrical axis of symmetry of fill valve 12 and fill valve housing 10.

One end of fill valve housing 10 is adapted to sealingly engage the pipe 14 to be tested. The end of fill valve housing 10 so adapted possesses large, thick pressure retaining housing walls 15 designed to withstand the high hydraulic pressure utilized to test the strength of the pipe 14. As shown in FIGS. 1 and 2, the pressure retaining housing walls 15 of fill valve housing 10 enclose an approximately cylindrically shaped chamber 16. Said chamber 16 is adapted to receive and contain the end of fill valve 12 which controls the flow of hydraulic fluid into the pipe 14.

The ends of the pressure retaining housing walls 15 are adapted to receive the pipe 14 to be tested. The surface of the interior of the pressure retaining housing walls 15 which engage the pipe 14 is threaded to receive the male end of the pipe 14. The female end of the pipe 14 is sealingly engaged by a plug (not shown) during the testing process. During the initial stages of the testing process, the fill valve housing 10 is sealingly engaged onto the male end of the pipe 14 by rotating the fill valve housing 10 with motive means (not shown). Rotation of the fill valve housing 10 causes the threads of the pipe 14 to engage the housing threads 18 and thereby seal the end of the pipe.

Referring to FIGS. 1 and 2, the body of the fill valve 12 generally comprises an elongated hollow right circular cylinder 20. The end of said cylinder farthest from the pipe 14 to be tested is open while the end of said cylinder closest to the pipe 14 to be tested is formed into a cylindrically symmetrical sealing head 22 which closes the end of the cylinder 20. Fill valve sealing head 22 has relatively thick walls in comparison to the walls of the elongated hollow cylinder 20 in order to contain the high pressure of the hydraulic fluid used during the testing process.

As shown in FIGS. 1 and 2, the external diameter of fill valve sealing head 22 at the point where elongated hollow cylinder 20 is joined to fill valve sealing head 22 is larger than the external diameter of elongated hollow cylinder 20. That portion of the pressure retaining housing walls 15 of housing 10 adapted to fit against the surface of fill valve sealing head 22 shall be referred to as the sealing head housing shoulder 38. When fill valve 12 is closed, fill valve sealing head 22 is seated against sealing head housing shoulder 38.

A cylindrically shaped aperture 30 in fill valve sealing head 22 penetrates and passes through sealing head 22 along the congruent cylindrical axis of symmetry of fill valve 12 and sealing head 22. As shown in FIGS. 1 and 2, an axial duct 32 adapted to fit snugly within said sealing head cylindrical aperture 30 passes through the length of the elongated hollow cylinder 20 and passes through and fits snugly within said sealing head cylindrical aperture 30. Axial duct 32 is firmly fixed by welding or other means within cylindrical aperture 30 of sealing head 22 in such a manner that no hydraulic fluid may pass through cylindrical aperture 30 of sealing head 22 outside the walls of axial duct 32.

The walls of the elongated hollow cylinder 20 comprising the body of fill valve 12 immediately behind fill valve sealing head 22 are perforated with a plurality of ports 34 for permitting the passage of low pressure hydraulic fluid from the interior of elongated hollow cylinder 20 into chamber 16. When fill valve 12 is moved forward laterally with respect to housing 10 to a position where fill valve sealing head 22 occupies the space within chamber 16 indicated in FIG. 2, then the walls of the elongated hollow cylinder 20 comprising the body of fill valve 12 immediately behind fill valve sealing head 22 extend into chamber 16 and expose said plurality of ports 34 to the interior of chamber 16. Then fill valve 12 is said to be open. When fill valve sealing head 22 is seated against sealing head housing shoulder 38 as in FIG. 1, no hydraulic fluid may flow through ports 34. Then fill valve 12 is said to be closed.

Means for sealing the interface between fill valve sealing head 22 and sealing head housing shoulder 38 when fill valve 12 is closed is provided so that hydraulic fluid may not leak into chamber 16 when fill valve 12 is closed. Such means may comprise an O-ring 40 set within a circularly shaped groove 41 cut into the body of fill valve sealing head 22 adjacent to and along the circumferential juncture between elongated hollow cylinder 20 and fill valve sealing head 22. A similar O-ring 42 is set within a similar groove 43 cut into and around the circumference of the body of elongated hollow cylinder 20, said groove 43 being located immediately behind and adjacent to the ports 34 as shown in FIGS. 1 and 2. The purpose of O-ring 42 and groove 43 is to provide means for preventing the leakage of hydraulic fluid from fill valve housing 10 through ports 34 and through the interface between fill valve housing 10 and elongated hollow cylinder 20 of fill valve 12.

As shown in FIGS. 1 and 2, the open end of elongated hollow cylinder 20 is adapted to be connected to means for introducing low pressure hydraulic fluid into the interior of fill valve 12. In the particular embodiment of the present invention the outer surface of the rear portion of elongated hollow cylinder 20 is threaded to engage the threaded interior surface of one port of a T-shaped low pressure hydraulic fluid joint 44. The second port of said T-shaped joint 44 is similarly threaded to receive a cylindrically shaped and externally threaded joint plug 46 which seals said second port of said joint 44. Joint plug 46 possesses a cylindrically shaped aperture along its cylindrical axis of symmetry. As shown in FIGS. 1 and 2, said aperture in said joint plug 46 is just large enough to permit high pressure axial duct 32 to snugly pass through said joint plug 46 whereby said axial duct 32 may be connected to a source of high pressure hydraulic fluid. The third port 48 in said T-shaped joint 44 serves as the inlet port for admitting low pressure hydraulic fluid into the interior of fill valve 12.

Turning now to the means for opening and closing fill valve 12, it is noted that more than one method may be employed to achieve the desired result. In one particular embodiment of the present invention a retaining spring 26 is employed to keep the fill valve in closed position. The body of fill valve 12 passes through said spring 26 and holds said spring 26 in position against housing 10 with annular flange 24 as shown in FIGS. 1 and 2. The expansive tension of spring 26 between annular flange 24 and the external surface of housing 10 retracts fill valve 12 from chamber 16 of housing 10 until fill valve sealing head 22 seats against sealing head housing shoulder 38 as shown in FIG. 1.

In operation fill valve 12 is opened against the retaining force of said spring 26 when the pressure differential between the interior of fill valve 12 and chamber 16 of housing 10 exceeds the retaining force of said spring 26. Initially, low pressure hydraulic fluid is introduced via inlet port 48 to fill the interior of fill valve 12. Since chamber 16 of housing 10 and the interior of pipe 14 are initially devoid of hydraulic fluid, the initial pressure differential equals the pressure on the low pressure hydraulic fluid minus the pressure of the atmosphere. Retaining spring 26 initially restrains the lateral motion of fill valve 12 into chamber 16. However, as the hydraulic pressure on the low pressure hydraulic fluid in fill valve 12 is increased, the pressure differential grows until the restraining force of retaining spring 26 is overcome. Then, compressing said spring 26, fill valve 12 moves laterally into chamber 16 exposing the fill valves ports 34 and permitting the low pressure hydraulic fluid to enter chamber 16 and pipe 14 through said ports 34. When said chamber 16 and pipe 14 are full of said hydraulic fluid, the aforementioned pressure differential drops to zero, thereby causing the retaining force of spring 26 to once again close fill valve 12.

Fill valve 12 may also be opened and closed as shown in FIG. 3. In this particular embodiment of the present invention, the motive means for moving fill valve 12 comprises a hydraulically operated piston 50. The reciprocal linear motion of said piston 50 is coupled to fill valve 12 via a pivot arm 52 disposed to pivot about a fixed pivot 54. As shown in FIG. 3, fill valve 12 remains in closed position when piston 50 is retracted within piston cylinder 56. As piston 50 is hydraulically extended from piston cylinder 56, pivot arm 52, which is pivotally connected to piston 50, pivots about fixed pivot 54 causing the T-shaped joint 44, to which said pivot arm 52 is also pivotally connected, to move forward, thereby moving fill valve 12 into open position. Said open position is shown in dotted outline in FIG. 3. When chamber 16 and pipe 14 have been filled with hydraulic fluid, fill valve 12 may be closed by retracting piston 50 into piston cylinder 56, thereby reversing the aforementioned pivoting action. Obviously, the piston may also be connected directly to fill valve 12 thereby obviating the need to use a pivot 54.

What is claimed is:

1. An apparatus for supplying fluid for hydraulic testing of pipe comprising:

housing means sealingly connectible to a pipe to be hydraulically tested, said housing means possessing an internal chamber which communicates with the interior of said pipe when said housing means and pipe are connected;

valve means within said housing means for admitting a first hydraulic fluid for hydraulic testing into said chamber of said housing means;

valve control means for opening or closing said valve means; and conduit means within said valve means for admitting a second hydraulic fluid for hydraulic testing into said chamber of said housing means, said second hydraulic fluid admitted by said conduit means being under greater hydraulic pressure than said first hydraulic fluid admitted into said chamber by said valve means.

2. An apparatus as in claim 1 wherein said valve means comprises:

an elongated hollow sleeve having perforations, said sleeve being slidably disposed within a hollow portion of said housing means which communicates with said chamber of said housing means, said sleeve having at least one perforation near the end of said sleeve that first enters said chamber of said housing means when said sleeve is caused to be slidably extended into said chamber;

a sealing head attached to said end of said sleeve which closes said end of said sleeve; and means for preventing fluid from passing from the interior of said sleeve into said chamber of said housing means through one or more perforations in said sleeve and through the interface between said sleeve and said housing means when said sleeve is not extended into said chamber of said housing means.

3. An apparatus as in claim 2 wherein said sealing head attached to said elongated hollow sleeve comprises a flanged body contained within said chamber of said housing means, said flanged body possessing a flanged portion with external dimensions greater than the external dimensions of said elongated hollow sleeve where said body is attached to said elongated hollow sleeve.

4. An apparatus as in claim 3 wherein said valve control means comprises a spring for retracting said elongated hollow sleeve from said chamber of said housing means.

5. An apparatus as in claim 3 wherein said valve control means comprises a pivot arm pivotally connected to said elongated hollow sleeve for longitudinally moving said elongated hollow sleeve into or out of said chamber of said housing means.

6. An apparatus as in claim 3 wherein said valve control means comprises a hydraulic piston and cylinder directly connected to said elongated hollow sleeve for longitudinally moving said elongated hollow sleeve into or out of said chamber of said housing means.

7. An apparatus as in claim 2 wherein said conduit means comprises a hollow duct which passes longitudinally through said elongated hollow sleeve and through said sealing head to communicate with said chamber of said housing means.

8. An apparatus as in claims 2, 3, 4, 5 or 6 wherein said means for preventing fluid from passing from the interior of said elongated hollow sleeve into said chamber of said housing means through one or more perforations in said sleeve and through the interface between said sleeve and said housing means when said sleeve is not extended into said chamber of said housing means comprises O-rings located within said elongated hollow sleeve and said sealing head.

* * * * *